(12) United States Patent
Mao et al.

(10) Patent No.: US 9,587,215 B2
(45) Date of Patent: Mar. 7, 2017

(54) DEVICES, SYSTEMS AND METHODS FOR AUTOMATED TRANSFER OF A SAMPLE

(71) Applicant: General Electric Company, Schenectady, NY (US)

(72) Inventors: Ying Mao, Niskayuna, NY (US); Kenneth Roger Conway, Clifton Park, NY (US); Weston Blaine Griffin, Niskayuna, NY (US); Reginald Donovan Smith, Schenectady, NY (US); Evelina Roxana Loghin, Rexford, NY (US); Vandana Keskar, Niskayuna, NY (US); Chengkun Zhang, Rexford, NY (US); Zhipeng Zhang, Cupertino, CA (US)

(73) Assignee: General Electric Company, Niskayuna, NY (US)

( * ) Notice: Subject to any disclaimer, the term of this patent is extended or adjusted under 35 U.S.C. 154(b) by 362 days.

(21) Appl. No.: 14/453,683

(22) Filed: Aug. 7, 2014

(65) Prior Publication Data
US 2016/0040114 A1    Feb. 11, 2016

(51) Int. Cl.
| | |
|---|---|
| *C12M 1/26* | (2006.01) |
| *C12M 1/34* | (2006.01) |
| *A01N 1/02* | (2006.01) |
| *B01L 7/00* | (2006.01) |
| *C12M 1/00* | (2006.01) |

(52) U.S. Cl.
CPC ............ *C12M 33/00* (2013.01); *A01N 1/0268* (2013.01); *B01L 7/00* (2013.01); *C12M 33/04* (2013.01); *C12M 41/12* (2013.01); *C12M 45/20* (2013.01); *B01L 2300/1827* (2013.01); *C12M 1/26* (2013.01); *C12M 45/22* (2013.01)

(58) Field of Classification Search
CPC ......... C12M 45/22; C12M 33/00; C12M 1/26
See application file for complete search history.

(56) References Cited

U.S. PATENT DOCUMENTS

| | | | |
|---|---|---|---|
| 3,884,765 | A | 5/1975 | Wilkins et al. |
| 6,821,773 | B1 | 11/2004 | Newberg |
| 7,629,167 | B2 | 12/2009 | Hodge et al. |
| 7,646,200 | B2 | 1/2010 | Slade et al. |
| 8,448,674 | B2 | 5/2013 | Py |
| 2008/0240998 | A1 | 10/2008 | Urbahn et al. |
| 2009/0291604 | A1 | 11/2009 | Park et al. |

(Continued)

FOREIGN PATENT DOCUMENTS

WO    2014013037 A1    1/2014

OTHER PUBLICATIONS

PCT Search Report and Written Opinion issued in connection with corresponding PCT Application No. PCT/EP2015/068037 on Nov. 25, 2015.

(Continued)

*Primary Examiner* — Jonathan Hurst
(74) *Attorney, Agent, or Firm* — Eileen B. Gallagher

(57) ABSTRACT

A coupling device configured to form a sample access assembly is provided. The sample access assembly is configured to house a sample. The coupling device includes a heating component and a separating component. Further, the separating component is configured to separate portions of first and second containers that form first and second compartments of the sample access assembly. Moreover, the heating component is configured to heat at least a portion of the sample.

23 Claims, 12 Drawing Sheets

(56) References Cited

U.S. PATENT DOCUMENTS

2010/0037415 A1    2/2010  Lansinger
2011/0036453 A1    2/2011  Ardenkjaer-Larsen et al.
2013/0172590 A1    7/2013  Pfeifer, III et al.
2014/0026593 A1    1/2014  Velayudhan et al.

OTHER PUBLICATIONS

Medinstill, "Fillers", http://medinstill.com/fillers.php, p. 1, 2016.
Heidmann et al., "A new seed-train expansion method for recombinant mammalian cell lines.", Biotechnology Unit, Bayer Corporation, Berkeley, CA, USA., vol. 38, Issue 1-3, 2002; 10 Pages.

DEVICES, SYSTEMS AND METHODS FOR AUTOMATED TRANSFER OF A SAMPLE

BACKGROUND

Embodiments of the present specification relate to sample transfer, and more particularly to automated sample transfer.

In manufacturing of recombinant proteins from mammalian cells, seed train expansion of cryo-preserved cells is a significant step required to initiate a new production campaign. This scale-up process or seed train expansion is significant since the quality of an inoculum often determines the success of the production campaign.

Typically, in a seed train expansion process, cells (such as cells for protein therapies) are initially cultured from a small volume (e.g., 1-ml or more) of a cryo-preserved sample. In an example, the sample to be cryo-preserved is placed in a cryo-vial and cooled down to a cryo cooling temperature of about $-80°$ C. or below to preserve the cells in the sample. Further, when required for inoculation, a small volume of about 1.0 ml to about 5.0 ml of the cryo-preserved sample is thawed to obtain a suspension of cells in the cryo-vial. Subsequently, the thawed sample cells are transferred into traditionally used culture vessels, such as T-flasks or spinner flasks. Additionally, the culture vessels are routinely incubated in a $CO_2$-controlled incubator.

Further, the cells in the culture vessels are mixed with a growth medium to facilitate cell growth. The suspension of the cells is sub-cultivated based on cell growth into an additional culture vessel of the same size or larger cell culture vessels. As the cells grow in quantity, the cells are transferred to increasingly larger volume culture vessels with more growth medium. This process of adding growth medium, cell transfer and cell growth continues until a determined cell mass is obtained. When the determined cell mass is accumulated, the cell suspension is collected and used to inoculate a bioreactor that may be used to start a new production campaign. In one example, the determined cell mass may be used to inoculate the production in vessels such as WAVE™ Bag and Xcellerex™ bioreactors.

Typically, the seed train expansion process requires complex manual operations and use of a plurality of culture vessels, resulting in increased probability of contamination of the cells. In addition, campaign-to-campaign variability of the seed train expansion process may result from the lack of active pH or dissolved oxygen and other similar indicators for control during scale-up.

Usually, the seed train expansion process needs to be carried out by a skilled operator. In initial stages of the cell culture and expansion, the operator needs to thaw the cryo-vial in a water bath or a bead bath. Additionally, the operator needs to decontaminate the outer surface of the vial. By way of example, surface decontamination of the cryo-vial may be performed by spraying chemicals, such as ethanol or bleach solutions. After surface decontamination, the cryo-vial is opened in a laminar hood. Further, a pipette is used to recover the inoculum sample from the cryo-vial and transfer the sample to a flask that is pre-filled with a determined amount of growth medium. Subsequently, the flask is placed into an incubator to complete the initial cell culture operation procedure. Accordingly, the existing process and the set-up associated with the seed train expansion process to initiate cell culture from a cryo-preserved sample of cells are both labor and infrastructure intensive.

BRIEF DESCRIPTION

In accordance with aspects of the present specification, a coupling device configured to form a sample access assembly using first and second containers is provided. The sample access assembly includes a first compartment and a second compartment. Further, the sample access assembly is configured to house a sample. The coupling device includes a heating component configured to heat at least a portion of the sample. Further, the coupling device includes a separating component configured to separate at least a portion of the first container and at least a portion of the second container from remaining portions of the first and second containers to form the first and second compartments of the sample access assembly. Moreover, the coupling device is configured to transfer at least a portion of the sample while maintaining a sterile environment for the sample at least during coupling of the first and second compartments.

In accordance with another aspect of the present specification, an automated system for sample transfer is provided. The automated system includes a coupling device and a collection device operatively coupled to the coupling device. The coupling device is configured to form a sample access assembly using first and second containers. The sample access assembly includes a first compartment and a second compartment. Further, the sample access assembly is configured to house a sample. The coupling device includes a heating component configured to heat at least a portion of the sample. Further, the coupling device includes a separating component configured to separate at least a portion of the first container and at least a portion of the second container from remaining portions of the first and second containers to form the first and second compartments of the sample access assembly. Moreover, the coupling device is configured to transfer at least a portion of the sample while maintaining a sterile environment for the sample at least during coupling of the first and second compartments. Also, the automated system includes a collection device operatively coupled to an outlet passage of the second compartment to receive at least a portion of the sample.

In accordance with yet another aspect of the present specification, a method for automated sample transfer is provided. The method includes providing a coupling device having first and second holder units. The method further includes disposing a first container having a sample in the first holder unit of the coupling device, and disposing a second container having an inlet passage and an outlet passage in the second holder unit of the coupling device. Additionally, the method includes separating at least a portion of the first container and at least a portion of the second container from remaining portions of the first and second containers to form first and second compartments. The method also includes coupling the first and second compartments to form a sample access assembly, and heating at least a portion of the sample to a determined temperature. Further, the method includes transferring at least a portion of the sample from the sample access assembly to a collection device.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Embodiments of the present specification relate to systems and methods for automated sample transfer. In certain embodiments, the systems and methods for automated sample transfer may form part of seed train expansion for cells. Further, some of these embodiments may be used to provide systems and methods for automated inoculum transfer of cryo-preserved sample cells to a collection device, such as, but not limited to, a culture vessel. In one example, population of mammalian cells may be transferred using the systems and methods of the present specification.

Figure 1:
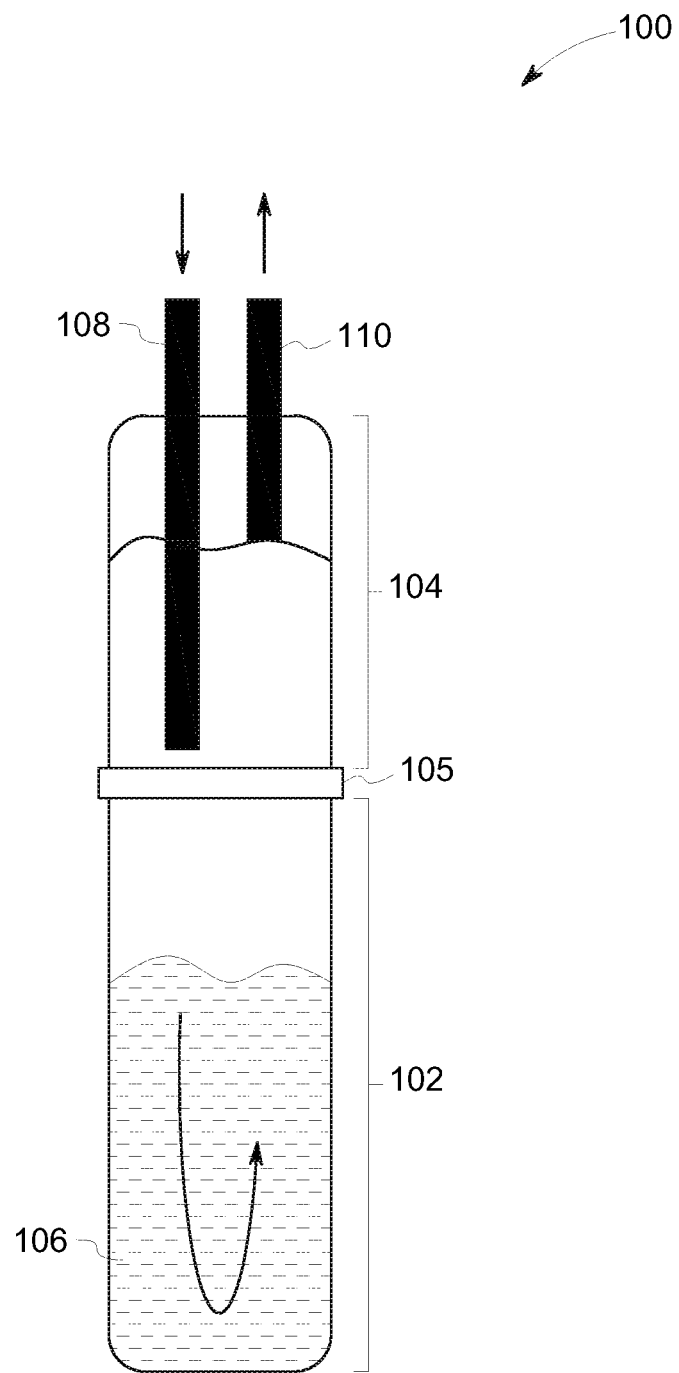
FIG. 1 is a schematic representation of an exemplary sample access assembly, in accordance with aspects of the present specification.

FIG. 1 is a schematic representation of a sample access assembly 100 of the present specification. In one embodiment, the sample access assembly 100 may be formed and employed in an automated system for sample transfer. In a particular embodiment, the sample access assembly 100 may be both formed as well as employed in the automated system for carrying out seed train expansion in an automated manner. Further, as described in detail herein, a portion of the sample access assembly 100 may be formed from at least a portion of a cryo-vial. In particular, a portion of the cryo-vial configured to house the sample may form part of the sample access assembly 100.

In the illustrated embodiment, the sample access assembly 100 includes a first compartment 102 and a second compartment 104. The first compartment 102 may be configured to receive a sample 106. In one embodiment, the first compartment 102 may be a portion of a standard cryo-vial and the second compartment 104 may be a portion of a similarly sized tube. Further, the second compartment 104 may be operatively coupled to the first compartment 102 such that the first and second compartments 102 and 104 are in fluidic communication with one another.

In certain embodiments, an automated system employing the sample access assembly 100 may be configured to operate with minimal operator intervention. In particular, once the sample 106 is disposed in the automated system by way of the first compartment 102, and the automated system is powered on, the system may be configured to carry out thawing of the sample, accessing the sample by coupling the first and second compartments 102 and 104 to create the sample access assembly 100, and transferring of the sample without further operator intervention.

In one embodiment, the first and second compartments 102 and 104 may be coupled using a joint 105. Moreover, in one embodiment, the joint 105 may be a fusion joint. In a non-limiting example, the joint 105 may be formed by thermal fusion, chemical fusion, or both. In one embodiment, the joint 105 may be formed by thermally fusing first and second compartments 102 and 104 together to form the sample access assembly 100. In a particular example, the joint 105 may be formed by thermally fusing interfaces of the first and second compartments 102 and 104. In one embodiment, the joint 105 may be a hermetically sealed joint to prevent the sample 106 from being contaminated.

Further, in the illustrated embodiment, the second compartment 104 may include an inlet passage 108 and an outlet passage 110. Moreover, in the sample access assembly 100, the sample 106 disposed in the first compartment 102 may be accessible via the inlet and/or outlet passages 108 and 110 of the second compartment 104. Accordingly, the sample access assembly 100 may be used to house, access and transfer the sample 106. Also, in one embodiment, the sample access assembly 100 may have more than one inlet and outlet passages 108 and 110. Further, the inlet and/or outlet passages 108 and 110 may have one or more ports.

In one embodiment, the sample access assembly 100 may be configured to transfer the sample 106 to a collection device (not shown in FIG. 1), such as a culture vessel, that is external to the sample access assembly 100. In this embodiment, the outlet passage 110 of the sample access assembly 100 may be coupled to the culture vessel. In one embodiment, the culture vessel may be used to culture the cells in the sample. In some embodiments, the sample access assembly 100 may be configured to receive a growth medium (not shown in FIG. 1) using the inlet passage 108. Further, the sample access assembly 100 may also be configured to transfer the sample 106 out of the sample access assembly 100 using the outlet passage 110.

In certain embodiments, lengths of the inlet and outlet passages 108 and 110 within the second compartment 104 may be varied depending on the desirable results. By way of example, the length of a portion of the inlet passage 108 disposed in the sample access assembly 100 may be more than the length of a portion of the outlet passage 110 disposed in the sample access assembly 100 so that an end of the inlet passage 108 is closer to the joint 105 relative to an end of the outlet passage 110 to facilitate mixing of the sample 106 and the growth medium. It may be noted that a mixture of the sample and the growth medium may be referred to as a "sample mixture."

Advantageously, the sample access assembly 100 may be configured to maintain a sterile environment for the sample 106 during processing of the sample. As used herein, the term "sterile environment" refers to an environment that is substantially free of undesirable microorganisms. In particular, the sample access assembly 100 may be configured to maintain the sterile environment for the sample 106 at least for the time duration when the sample 106 is disposed in the sample access assembly 100. Further, the sample access assembly 100 may be configured to maintain the sterile environment for the sample 106 at least for the time duration when the sample 106 is being transferred from the sample access assembly 100 to the collection device.

Figure 2:
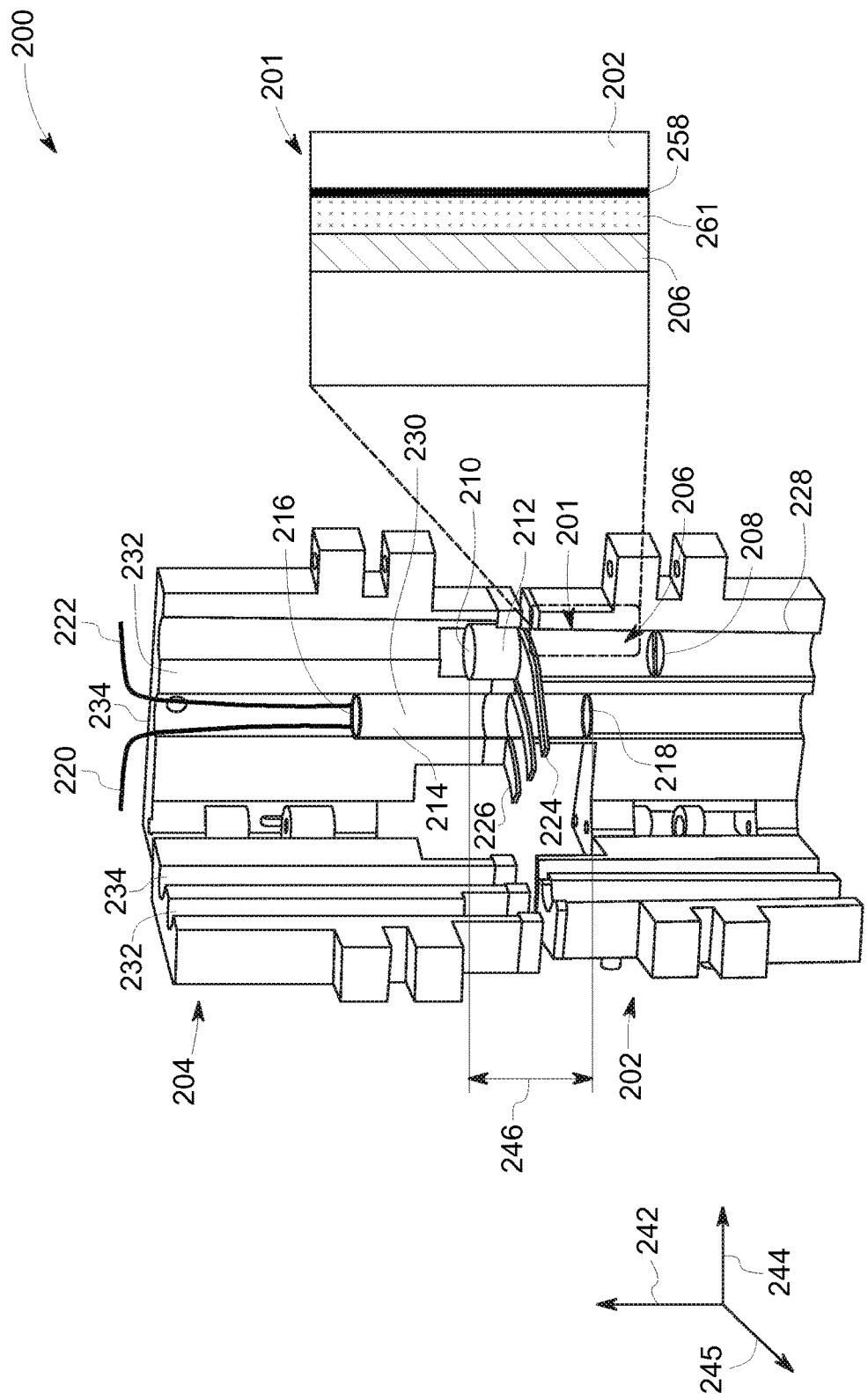
FIGS. 2-8 are schematic representations of exemplary methods of assembling the sample access assembly of FIG. 1 using a coupling device, in accordance with aspects of the present specification.

FIGS. 2-8 illustrate a coupling device 200 for forming a sample access assembly 260 (see FIG. 8) to facilitate transfer of a sample (not shown in FIG. 2). The coupling device 200 may form part of an automated system for sample transfer, such as an automated system illustrated in FIG. 11. Further, the coupling device 200 is configured to form the sample access assembly 260, where the sample access assembly 260 is configured to house at least a portion of the sample. In certain embodiments, the coupling device 200 includes a heating component 201 (see FIG. 2) and a separating component 203 (see FIGS. 3-8). In the illustrated embodiment, the coupling device 200 may also include a component position frame. In certain embodiments, the component position frame may be optional. The component position frame may be configured to provide mechanical integrity and robustness to the coupling device 200. Further, the component position frame may be configured to house and/or hold various disposable fluid path components. Additionally, the component position frame may include provisions to receive first and/or second containers 206 and 214. By way of example, an operator may dispose the first and/or second containers 206 and 214 in the coupling device 200 via the component position frame. Further, the component position frame may be configured to maintain relative positions of two or more components of the coupling device 200 both before and after formation of the sample access assembly 260.

In certain embodiments, the heating component 201 is configured to heat at least a portion of a sample, before and/or after formation of the sample access assembly 260. Further, the separating component 203 is configured to couple first and second compartments 266 and 268 (see FIGS. 7-8) to form the sample access assembly 260. In some embodiments, the coupling device 200 may be configured to transfer at least a portion of the sample while maintaining a sterile environment for the sample, for example during or after coupling of the first and second compartments. In one embodiment, a collection device (not shown in FIG. 2) for receiving the sample mixture may be disposed in the coupling device 200. In another embodiment, the collection device may be disposed outside the coupling device 200.

In the illustrated embodiment, the coupling device 200 includes a first holder unit 202 and a second holder unit 204 that is operatively coupled to the first holder unit 202. Further, it may be noted that FIG. 2 illustrates an embodiment where the coupling device 200 is open to illustrate details of the holder units 202 and 204 from within. FIGS. 3-8 illustrate exemplary steps of forming the sample access assembly 260 using the coupling device 200 illustrated in FIGS. 2-8.

In the illustrated embodiment of FIG. 2, the first holder unit 202 is configured to receive at least a portion of the first container 206. Further, the first container has a first side 208 and a second side 210. Moreover, the first and second sides 208 and 210 of the first container 206 may be configured to be closed. By way of example, the first container 206 may be a sample vial and the first side 208 of the vial may be closed and the second side 210 of the vial may have a cap 212. Non-limiting examples of the cap 212 may include a sealant film.

Also, the second holder unit 204 is configured to receive at least a portion of the second container 214. The second container 214 includes a first side 216 and a second side 218. The second container 214 may or may not have a substantial volume. In one embodiment, the second container 214 may be a vial, while in another embodiment the second container 214 may be a closed container without any substantial volume. Additionally, the second side 218 of the second container 214 may be at least partially closed. Further, the first side 216 of the second container 214 includes an inlet passage 220 and an outlet passage 222. In one embodiment, the inlet and outlet passages 220 and 222 may be inlet and outlet tubes. In a non-limiting example, the inlet and outlet passages 220 and 222 may be formed using dual lumen tubing. The inlet and outlet tubes 220 and 222 may be flexible or rigid tubes.

Although not illustrated in FIGS. 3-8, in some embodiments, before disposing the second container 214 in the second holder unit 204, the inlet passage 220 may be operatively coupled to a growth medium source, a pump, or both. In one embodiment, the inlet passage 220 may be coupled to the growth medium source via the pump, such as, but not limited to, a peristaltic pump. Additionally or alternatively, the peristaltic pump may also be coupled to the outlet passage 222. In particular, an end of the inlet passage 220 may be coupled to an outlet of the growth medium source and the pump may be operatively coupled between the growth medium source and the second container 214. Further, the pump may be configured to facilitate inflow of a desirable amount of the growth medium in the sample access assembly 260 at a determined rate. In some embodiments, the collection device may be pre-attached to the second container 214. In one embodiment, the collection device may be pre-coupled to and in fluidic communication with the second container 214 through the tubing of the outlet passage 222. In another embodiment, the collection device may be operatively coupled to the second container 214 immediately prior to use by the operator using proper aseptic techniques. Further, it may be noted that the collection device is a cell-culture compatible vessel that is configured to receive the sample mixture while maintaining a sterile environment for the sample. Non-limiting examples of the collection device may include a sterilized flask, a sterilized bioreactor, or both.

In certain embodiments, the first and second holder units 202 and 204 may include clamps or other similar structures for mechanically holding the first and second containers 206 and 214, respectively. However, the first holder unit 202, the second holder unit 204, or both may have one or more degrees of freedom with respect to each other. In a non-limiting example, the first and second holder units 202 and 204 may have three degrees of freedom with respect to each other. Further, the first and second holder units 202 and 204 may be configured to align and fuse portions of the first and second containers 206 and 214 to form the sample access assembly 260 while maintaining the sterile environment for the sample disposed in the first container 206.

In the illustrated embodiment, the first and second holder units 202 and 204 may include features 224 and 226 configured to hold the first and second containers 206 and 214, respectively. Further, the features 224 and 226 may be configured to retain the first and second containers 206 and 214 in their respective positions during loading of the containers 206 and 214 and closing of the holder units 202 and 204 after loading of the containers 206 and 214. By way of example, the features 224 and 226 may be configured to retain the first and second containers 206 and 214 in their respective slots 228 and 230 in the first and second holder units 202 and 204, respectively, during loading of the containers 206 and 214 and closing of the holder units 202 and 204. In the illustrated embodiment, the features are illustrated as being fork shaped elements, however, in alternative embodiments, the features 224 and 226 may have any other shape that is suitable to hold the first and second containers 206 and 214 in position. Further, the features 224 and 226 and the slots 228 and 230 may be configured to receive the first and second containers 206 and 214 of varying shapes and sizes. For example, easily operable adjustments may be provided to adjust the features 224 and 226 and/or the slots 228 and 230 to conform to physical dimensions of the first and second containers 206 and 214.

Further, the features 224 and 226 and the slots 228 and 230 (see FIGS. 3-4) may be configured to position the first and second containers 206 and 214 such that at least a portion of the first and second containers 206 and 214 may overlap in a first direction 242. Moreover, before being coupled together to form the sample access assembly 260, the first and second containers 206 and 214 may be disposed away from each other in a second direction 244. In the illustrated embodiment, the overlapping portions of the first and second containers 206 and 214 are generally represented by reference numeral 246.

In some embodiments, the features 224 and 226 may include several structures to enhance ergonomics and compatibility of the coupling device 200. By way of example, the fork-like shape of the features 224 and 226 may facilitate easy installation of the first and second containers 206 and 214 in the coupling device 200. In some of these embodiments, the fork is designed to accommodate vials of various diameters as well as cross-sectional geometries, such as, but not limited to, circular, square, rectangular, or any other geometrical or non-geometrical shape. Relative motion of the holder units 202 and 204 in the direction 242 is used to close the coupling device 200.

Figure 3:
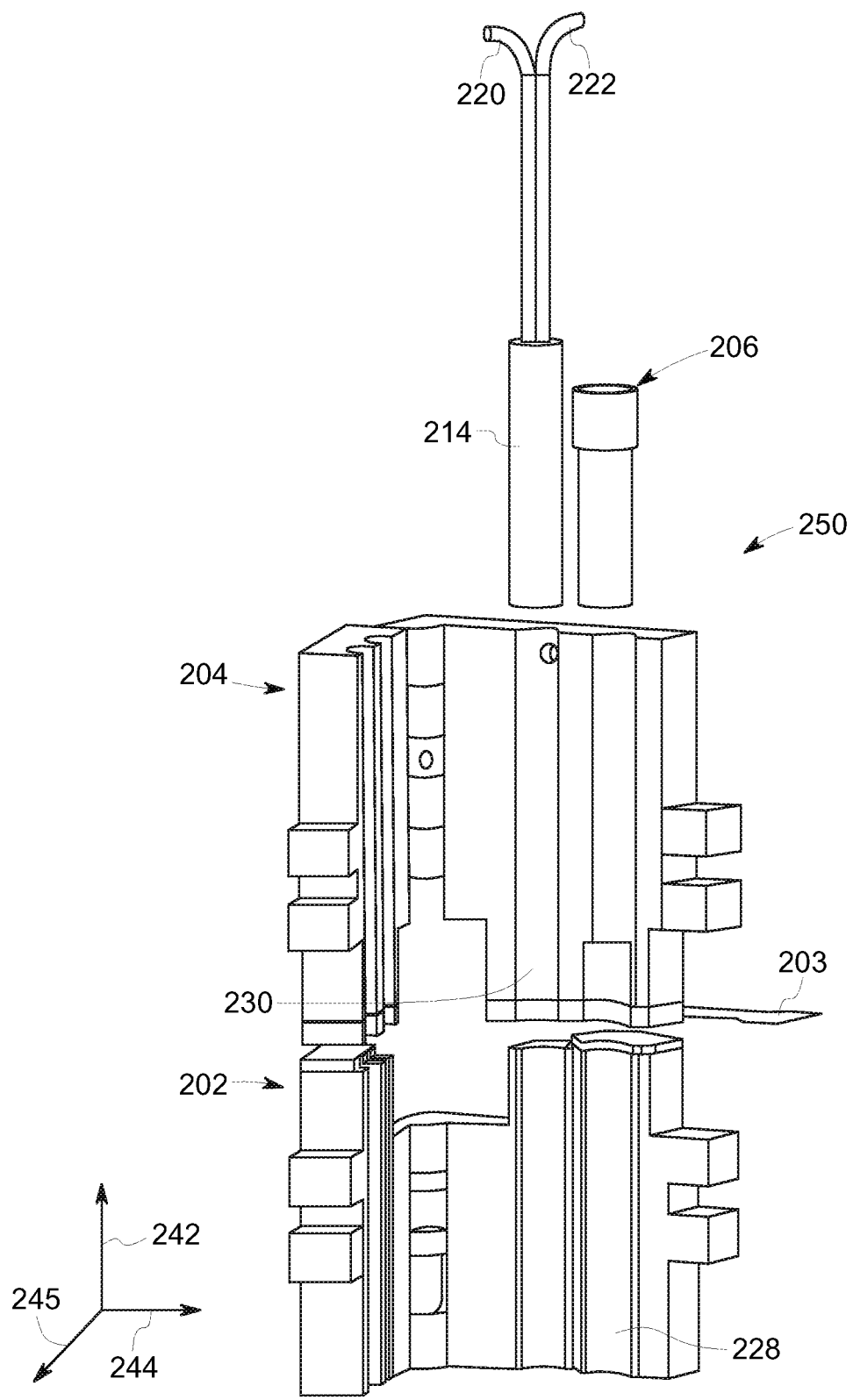
Figure 4:
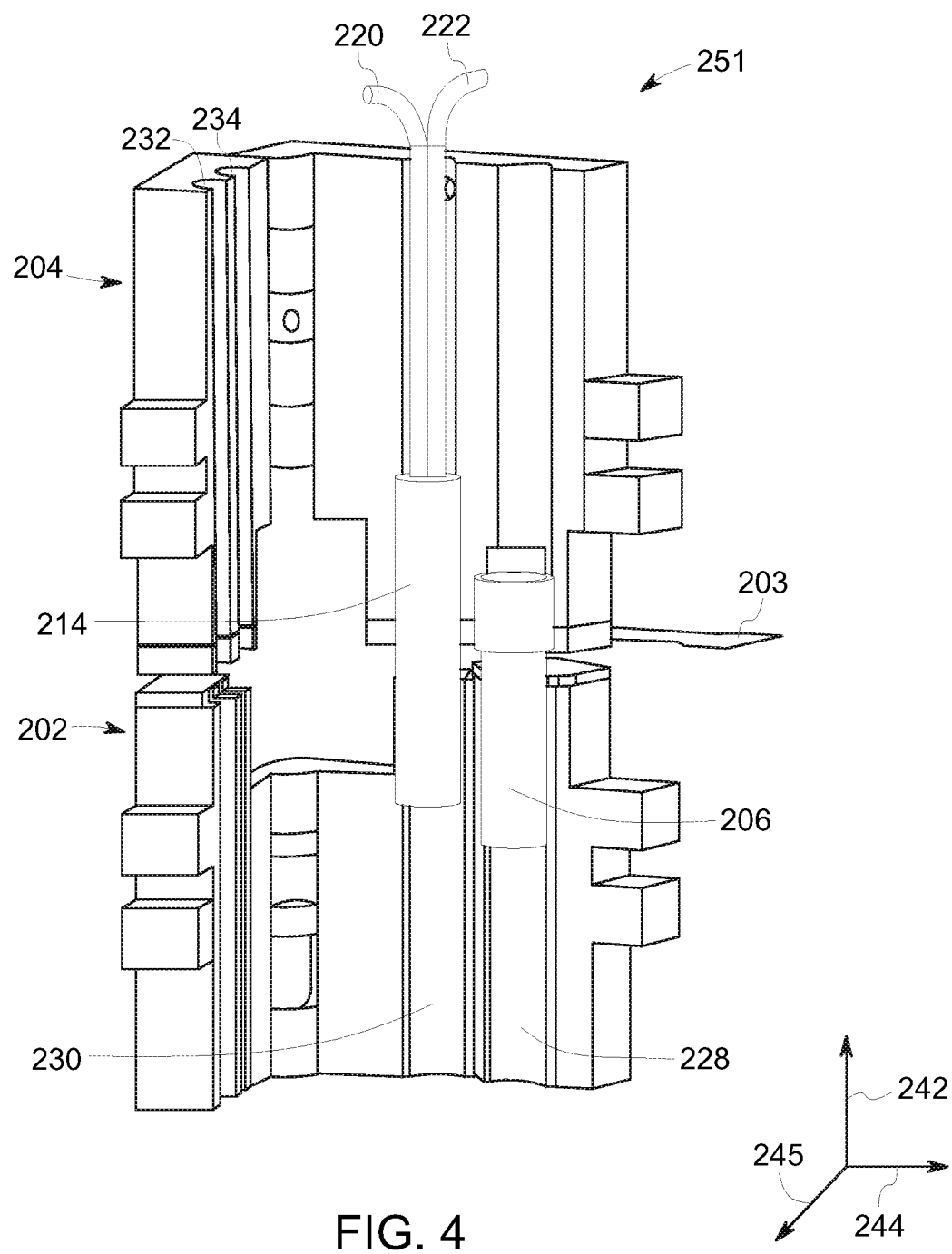

In one embodiment, the coupling device 200 may initially be in an open state in the beginning and the user may need to simply dispose or drop-in the first and second containers 206 and 214 in corresponding openings 232 and 234, and then close the coupling device 200 to realize loading procedure for the coupling device 200. FIGS. 2-4 illustrate the coupling device 200 in an open state, and FIGS. 5-8 illustrate the coupling device 200 in a closed state. During the loading procedure, the first and second containers 206 and 214 may be locked in correct locations automatically. In another embodiment, it may not be required to open and close the coupling device 200 to carry out the loading procedure. For example in this embodiment, the first and second containers 206 and 214 may be simply dropped in the coupling device 200 in the closed state of the coupling device 200 using the openings 232 and 234. In one embodiment, the first container 206 and the second container 214 and the may be disposed on a component position frame by the user at the time of use of the coupling device 200. In some embodiments, the first and second holder units 202 and 204 may be operatively coupled to one or more actuators, such as linear and/or rotary actuators, to facilitate movement of the first and second holder units 202 and 204 for operation of the coupling device 200.

In certain embodiments, the heating component 201 may be configured to heat at least a portion of the sample disposed in the first container 206 and/or a portion of the sample access assembly 260. In one example, the heating component 201 may be configured to thaw the sample disposed in the first container 206 and/or sample access assembly 260 to a determined temperature. Accordingly, the heating component 201 may be disposed in the first holder unit 202 such that the heating component 201 is operatively coupled to at least a portion of the first container 206. In one example where the first container 206 is a cryo-vial, in operation, the cryo-vial having the sample at a cryo-temperature may be directly disposed in the coupling device 200. The heating component 201 may then thaw the sample in the cryo-vial to a desirable temperature. Advantageously, the heating component 201 is configured to heat the frozen sample disposed in the first container 206 at a desirable heating rate. In a particular example, the heating component 201 is configured to rapidly thaw a cryo-preserved sample disposed in the cryo-vial.

In certain embodiments, the heating component 201 may include a multilayered structure as will be described in detail with respect to FIG. 10. The heating component 201 may be disposed around a portion of the first container 206. In the illustrated embodiment of FIG. 2, the heating component 201 includes a thin film heater 258 and a thermally conductive foam 261 disposed adjacent the first container 206. The thermally conductive foam 261 is configured to provide uniform heat flux on at least a portion of a surface of the first container 206. This uniform heat flux may be achieved by compliance in the thermally conductive foam 261 that facilitates elimination of air gaps between the thin film heater 258 and the surface of the first container 206. Further, in case of the thin film heater 258 being used as the heating component 201, the thermally conductive nature of the thermally conductive foam 261 helps reduce hot spots. Although not illustrated, it is envisioned that in some embodiments, another heating component may be similarly disposed around at least a portion of the second container 214. This other heating component disposed around the portion of the second container 214 may be configured to heat at least a portion of the growth medium prior to mixing of the growth medium with the sample. In one embodiment, the heating component 201 may be disposed at least in part in the slots 228 and 230. In one embodiment, where the heating component 201 includes two halves, the two halves of the heating component 201 may be disposed in the slots 228 and 230 present in two portions of the coupling device 200, such that when the coupling device 200 is closed, the two halves of the heating components 201 are disposed around at least a portion of the first container 206. Further, in some embodiments, the heating component 201 may be a battery operated heater or a chemical heater.

Additionally, in some embodiments, the separating component 203 may be configured to separate at least a portion of the first and second containers 206 and 214 to form the first and second compartments 266 and 268 of the sample access assembly 260. Additionally, the separating component 203 may be positioned such that the separating component 203 is aligned with or overlaps in the first direction 242 with the overlapping portions 246 of the first and second containers 206 and 214. Further, the separating component 203 may be configured to be placed in physical contact with the first and second containers 206 and 214 during formation of the sample access assembly 260. In a particular embodiment, the separating component 203 may be configured to be in physical contact with the first and second containers 206 and 214 simultaneously, almost simultaneously, or in quick succession. In some embodiments, the separating component 203 may be hinged so as to be able to at least partially rotate about a determined point or axis in the coupling device 200.

Also, in certain embodiments, the separating component 203 may be configured to be heated to a determined temperature. In some of these embodiments, the separating component 203 may be configured to be heated to the determined temperature by passing an electric current through portions of the separating component 203.

In some embodiments, the separating component 203 may be a blade. Further, the blade may have a continuous structure or a patterned structure. In one embodiment, the patterned structure may include a plurality of strips, wires, cables, or combinations thereof. Further, in some embodiments, the separating component 203 may include a laser beam. The laser beam may be used alone or in combination with the blade. Further, in some embodiments, a sterilizing environment may be provided within the coupling device 200 at the time of a separating action of the respective portions of the first and second containers 206 and 214 to form the first and second compartments 266 and 268 of the sample access assembly 260.

Further, the separating component 203 may have a mechanical strength and thickness suitable to render a non-warping characteristic to the blade. Advantageously, the non-warping characteristic of the separating component 203 along with a desirable temperature of the separating component 203 may result in clean cutting of the first and second containers 206 and 214 resulting in smooth interfaces at a point of contact of the blade and the first and second containers 206 and 214. As it may be noted, smooth interfaces or clean cutting of the first and second containers 206 and 214 facilitates enhanced fusion of the first and second containers 206 and 214 and provide hermetic sealing of the sample access assembly. In one embodiment, the separating component 203 may have a thickness in a range from about 0.01 inch to about 0.03 inch to about 0.03 inch. In another embodiment, 203 may be coated with polytetrafluoroethylene (PTFE), or other material to create a lubricious surface that may result in higher quality separation of the containers. Further, in these or other embodiments, the separating component 203 may be made of high temperature materials, such as, but not limited to, platinum, tungsten, nichrome, nickel (Alloy HX), or combinations thereof. In one embodiment, the separating component 203 may be made of an electrically conductive material, such as, but not limited to, tungsten, nichrome, nickel (Alloy HX), or combinations thereof. Moreover, in one embodiment, the separating component 203 may be heated and maintained at the determined temperature for up to a few seconds to sterilize the separating component 203.

Further, subsequent to heating the separating component 203, motion of the separating component 203 may be initiated to facilitate cutting the portions of the first and second containers 206 and 214 in a transverse direction for the first and second containers 206 and 214, also represented as the direction 245. In one embodiment, the separating component 203 may be used to almost simultaneously separate the overlapping portions 246 of the first and second containers 206 and 214 to form the first and second compartments. In one embodiment, the separating component 203 may be configured to cut the portions of the first and second containers 206 and 214 in a single swipe of the separating component 203.

In quick succession to the separating step, the first and second compartments 266 and 268 may be aligned. By way of example, the first and second holder units 202 and 204 having the first and second compartments 266 and 268 may be moved relative to each other to align the first and second compartments 266 and 268 to form the sample access assembly 260. For example, the first and second holder units 202 and 204 may be moved relative to each other in the second direction 244 to align the first and second compartments 266 and 268. Additionally, the first and/or second holder units 202 and 204 may be moved towards each other in the first direction 242 and pressed against each other to form a joint between the remaining portions of the first and second containers 206 and 214. In one embodiment, the joint may be a thermal joint that is formed due to melting and fusion of the materials of the first and second containers 206 and 214 at the interface of the first and second containers 206 and 214. Further, in one embodiment, the separating component 203 may be configured to retract before the joint is formed between the remaining portions of the first and second containers 206 and 214 or the first and second compartments 266 and 268 of the sample access assembly 260.

It may be noted that various motions, including the motion of the separating component 203, and the motion of the holder units 202 and 204 in one or more directions may occur simultaneously or with a minimal time lag to prevent exposure of the sample disposed in the first container 206 to the environment. In one embodiment, immediately after separation of the portions of the first and second containers 206 and 214, one or both the holder units 202 and 204 may commence to move relative to each other to align the portions of the first and second containers 206 and 214.

In certain embodiments, the coupling device 200 may have three actuated degrees of freedom used to perform four main operations, namely (1) motion of the separating component 203 in the third direction 245 so as to separate the first and second containers, (2) an alignment motion of the first and second containers 206 and 214 realized by the motion of the first and second holder units 202 and/or 204 in the second direction 244, (3) a motion of the separating component 203 in the third direction 245, and (4) a coupling motion of the first and second holder units 202 and 204 in the first direction 242 used to form a mechanical coupling or joint between the first and second containers 206 and 214. In one embodiment, the operations (3) and (4) may be performed simultaneously. In some embodiments, after installation of the first and second containers 206 and 214, the operator may switch on the coupling device 200 to start the automated transfer procedure of the sample mixture.

In some embodiments, alignment motion of the holder units 202 and 204 may be used to align the portions of the first and second containers 206 and 214 to form the sample access assembly 260. In some embodiments, after the alignment motion of the holder unit 202 and 204, the first and second containers 206 and 214 may dwell on the separating component 203 for some time to enhance bonding between interfaces of the first and second compartments of the first and second containers 206 and 214. In particular, the first and second containers 206 and 214 may dwell on the separating component 203 for a desirable time period to allow sufficient amount of plastic at the interface of the first and second compartments to melt, thereby increasing the material available for bonding the first and second compartments. Subsequently, coupling motion of the holder units 202 and 204 may be used to move the holder units 202 and 204 towards each other in the first direction 242 to form a joint between the portions of the first and second containers 206 and 214. Further, this coupling motion of the holder units 202 and 204 may be performed while the separating component is moving away from the first and second containers 206 and 214 after separating portions of the first and second containers 206 and 214.

Advantageously, one or more components of the coupling device 200 are disposable in nature, thereby reducing the chances of contamination of two or more samples. Further, the coupling device 200 of the present application is configured to effectively and efficiently thaw, access as well as transfer the contents (sample) from the first container 204, such as a cryo-vial, in a sterile manner to a desirable collection device in a time efficient manner with minimal user intervention. Further, the coupling device 200 is configured to transfer the sample mixture into a bioreactor in a sterile manner while being disposed in any non-sterile environment that may lie outside bounds of a biological safety cabinet.

Figure 5:
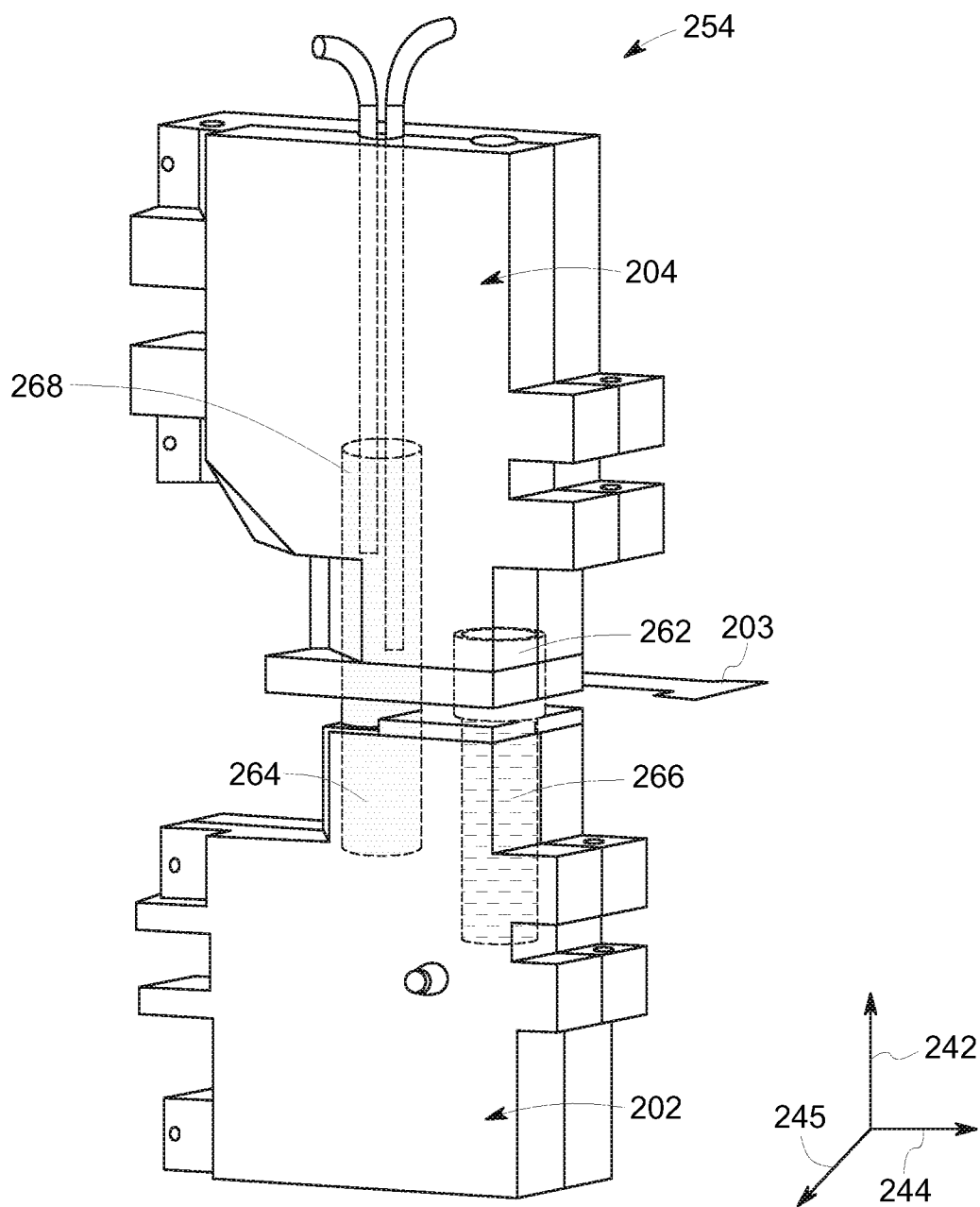
Figure 6:
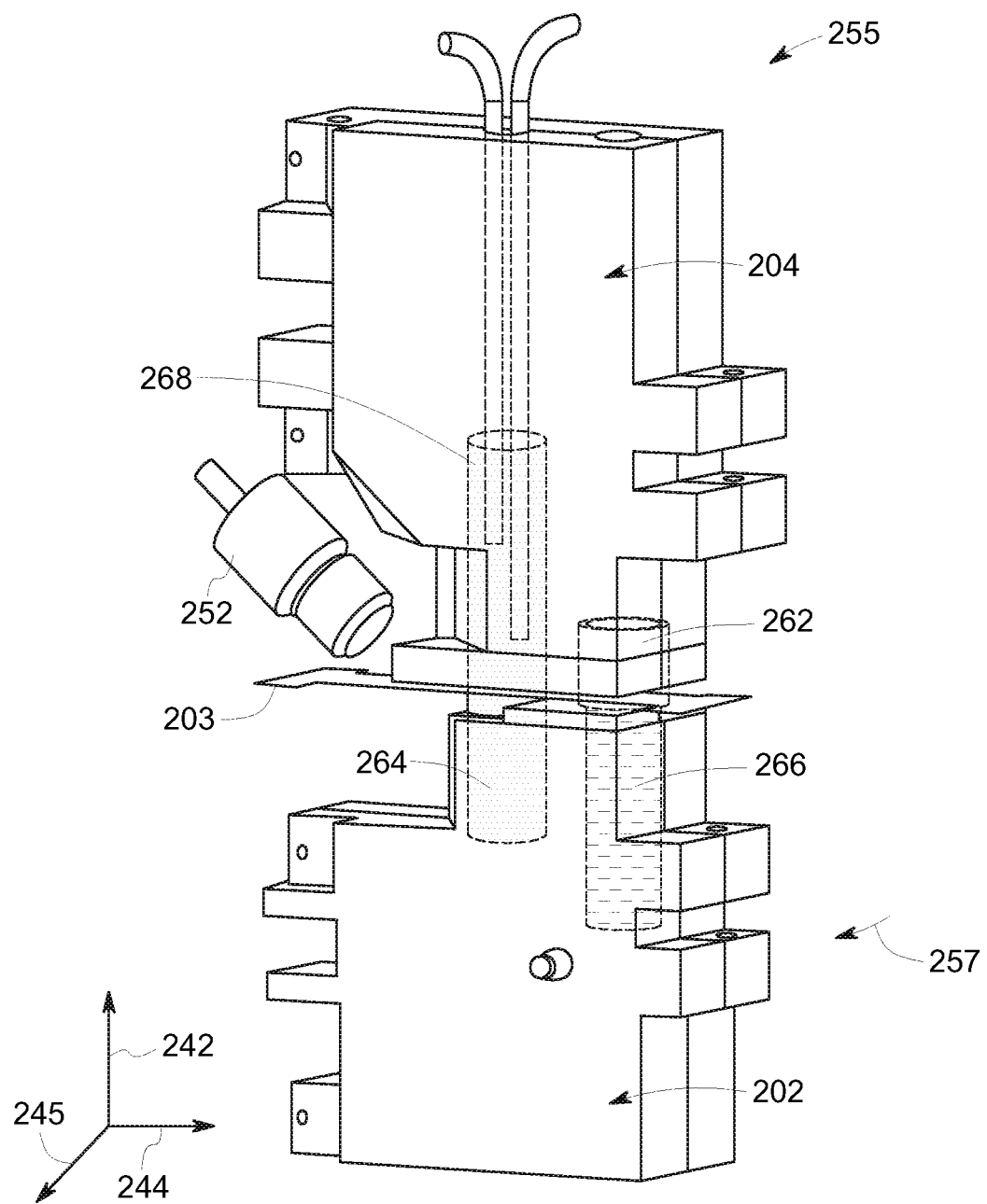

FIG. 3 illustrates an embodiment 250 of the coupling device 200 of FIG. 2 prior to disposing the first and second containers 206 and 214 in their respective slots 228 and 230 of the coupling device 200. As illustrated, the slot 230 is configured to receive the second container 214. Further, as illustrated in the embodiment 251 of FIG. 4, the slot 228 is configured to receive the first container 206. The relative positions of the separating component 203 and the first and second containers 206 and 214 is such that a motion of the separating component 203 blade in the direction 245 separates portions of the first and second containers 206 and 214 to form compartments 266 and 268 of the sample access assembly 260. As illustrated in FIG. 5, after loading the first and second containers 206 and 214, the coupling device is closed. The closed coupling device is generally represented by reference numeral 254. Referring now to FIG. 6, in the illustrated embodiment 255, a temperature of the separating component 203 is monitored using a temperature sensor 252. To ensure a sterile environment for the sample, the separating component 203 is maintained at a high temperature as well as in close contact with the first and second containers 206 and 214 during the separation of the portions of the first and second containers 206 and 214.

A swiping action of the separating component 203 in a direction represented generally by arrow 257 is performed to separate out portions 262 and 264 of the first and second containers 206 and 214 from portions 266 and 268 of the first and second containers 206 and 214, respectively.

Figure 7:
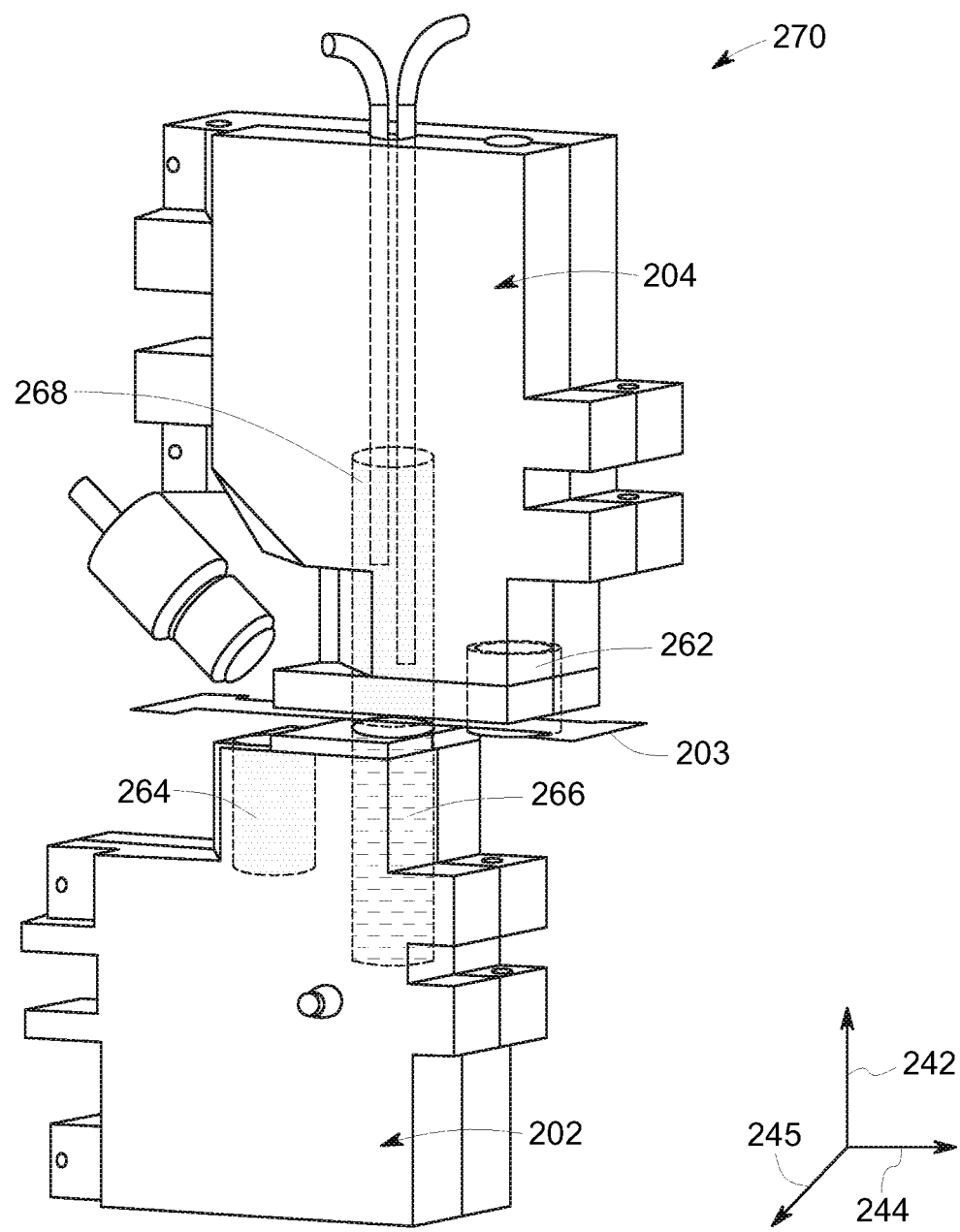

Referring to the embodiment 270 of FIG. 7, after separating component 203 separates out portions of the first and second containers 206 and 214, the portions 266 and 268 of the first and second containers 206 and 214 are aligned with each other. In the illustrated example, the first and second holder units 202 and 204 may be moved relative to each other in the second direction 244 to align the portions 266 and 268 that form the first and second compartments of the sample access assembly 260.

Figure 8:
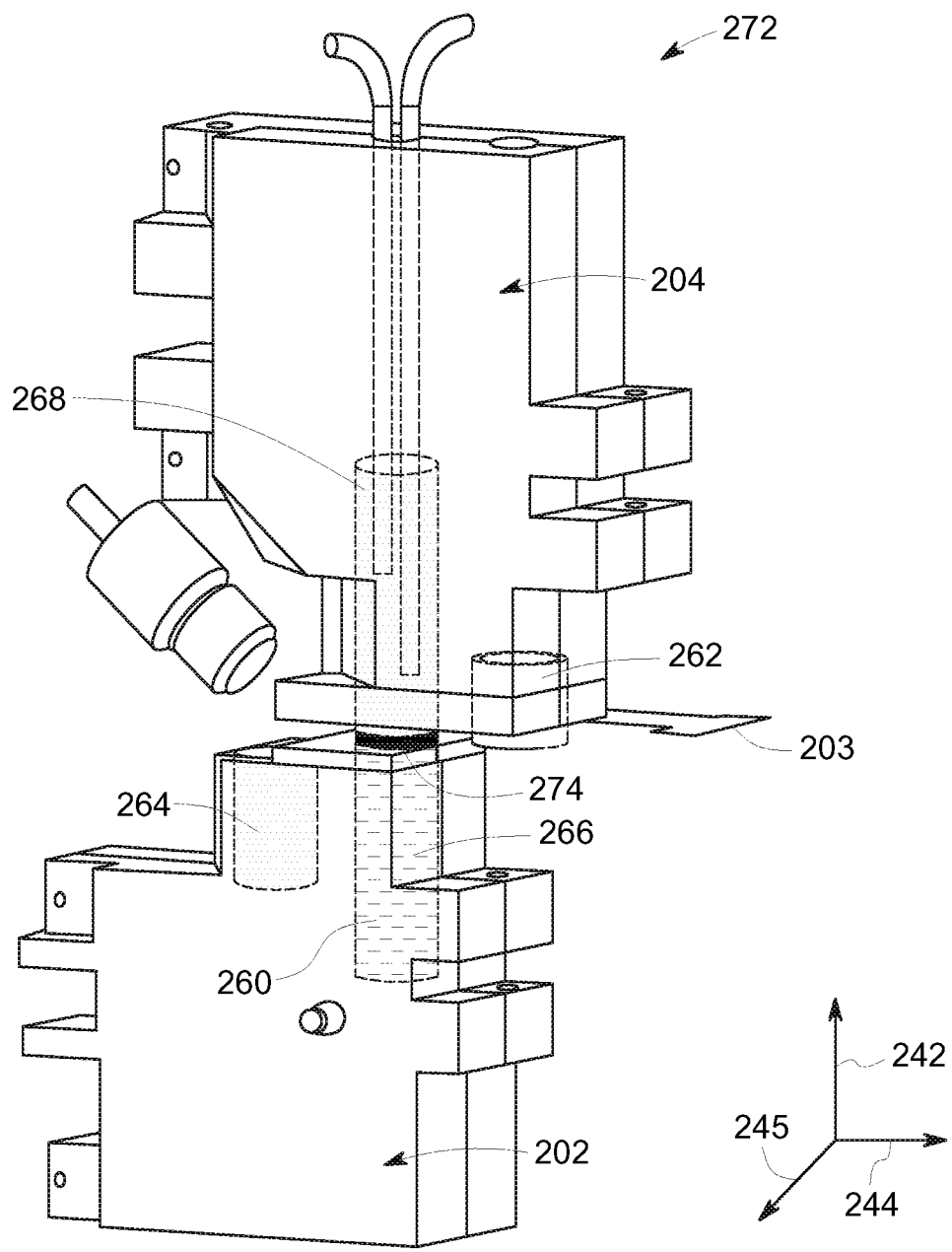

Further, as illustrated in the embodiment 272 of FIG. 8, the first and/or second holder units 202 and 204 may be moved towards each other in the first direction 242 and pressed against each other to form a joint between the portions 266 and 268 of the first and second containers 206 and 214 to form the sample access assembly 260 having first and second compartments 266 and 268. In one embodiment, the joint may be a thermal joint 274 that is formed due to melting and fusion of the materials of the first and second containers 206 and 214 at the interface of the portions 266 and 268 of the first and second containers 206 and 214. It may be noted that after the separating action is completed and before forming the thermal joint 274, the separating component 203 may be retracted as illustrated in FIG. 8. Optionally, the portions 262 and 264 of the first and second containers 206 and 214 may be removed from the coupling device 200 using mechanical methods or other methods.

Figure 9:
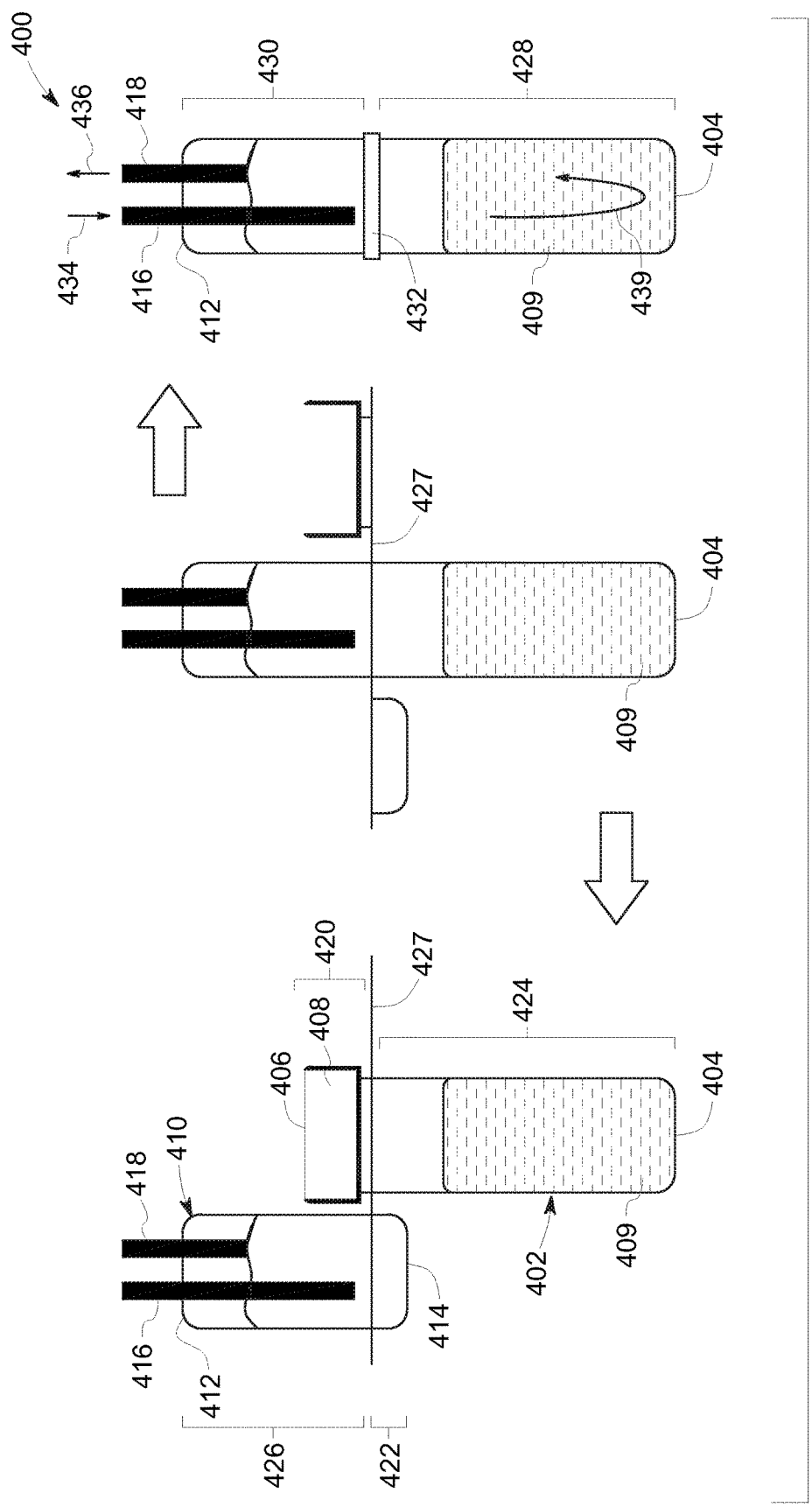
FIG. 9 is a schematic representation of a method of assembling a sample access assembly, in accordance with aspects of the specification.

FIG. 9 is a schematic representation of a method of assembling a sample access assembly 400, such as the sample access assembly 100 of FIG. 1. In the illustrated embodiment, a sample access assembly 400 is assembled from portions of a first container 402 and a second container 410. Further, the first container 402 includes a first side 404 and a second side 406. Further, the first side 404 of the first container 402 is closed, whereas, the second side 406 of the first container 402 is configured to open or close as required. By way of example, the second side 406 may include an open end and a corresponding lid 408, where the lid 408 is configured to be disposed on the open end to close the first container 402. In one example, the first container 402 may be a vial with a removable threaded cap. In one embodiment, the lid 408 may be removed or detached to dispose a sample 409 in the first container 402. Subsequently, the lid 408 may be placed on the first container to close the second end 406 of the first container 402. In one example, the first container 402 may be a cryo-vial, a polymer tube, or both.

Further, the second container 410 may include a first side 412 and a second side 414. The first and second sides 412 and 414 of the second container 410 may be closed. Moreover, the first side 412 of the second container 410 may include at least an inlet passage 416 and an outlet passage 418. In some embodiments, a portion of the inlet passage 416 disposed inside the second container 410 may be longer than a portion of the outlet passage 418 that is disposed inside the second container 410. In some embodiments, the second container 410 may be pre-sterilized before coupling the second container 410 and the first container 402. The second container 410 may be a tube, a vial, or any other container that is configured to provide an interface that may be configured to be coupled to the first container 402.

Further, the inlet and outlet passages 416 and 418 may be sterilized before coupling the first container 402 and the second container 410. Additionally, in one embodiment, the second container 410 may be coupled to one or more other components before coupling portions of the first and second containers 402 and 410 to form the sample access assembly 400. In one embodiment, these other components may be external to the sample access assembly 400. By way of example, the second container 410 may be coupled to a culture vessel, such as a bioreactor configured to collect the sample, or a pump configured to pump in a growth medium in the sample access assembly 400. In one embodiment, the inlet passage 416 of the second container 410 may be operatively coupled to a growth medium source (not shown in FIG. 9) before coupling the first container 402 and the second container 410. Further, the outlet passage 418 may be coupled to a collection device (not shown in FIG. 9) before coupling the first container 402 and the second container 410. Non-limiting examples of the collection device may include a flask or a bioreactor.

In one embodiment, the sample access assembly 400 may be a disposable device. Further, as illustrated, the sample access assembly 400 may be formed by separating respective portions 420 and 422 of the first and second containers 402 and 410 disposed closer to the respective second sides 406 and 414 of the first and second containers 402 and 410 while subsequently coupling interfaces of remaining portions 424 and 426 of the first and second containers 402 and 410, respectively, to form the sample access assembly 400.

Also, in one embodiment, the portions 424 and 426 of the first and second containers 402 and 410, respectively, may be moved relative to each other to align the remaining portions 424 and 426 of the first and second containers 402 and 410 with respect to each other such that the remaining portions 424 and 426 of the first and second containers 402 and 410 are disposed on one another. Although in the illustrated embodiment, the first and second containers 402 and 410 are shown to have similar cross-sectional area throughout, however, in some embodiments, only interfaces of the remaining portions 424 and 426 of the first and second containers 402 and 410 that come in contact to form the sample access assembly 400 may have similar cross-sections. By way of example, the first container 402 may be in the shape of a bag with a spout like structure disposed at a second side of the bag, where this spout like structure may have a cross-section similar to the cross-section of an interface of the second container 410. In a particular embodiment, the first container 402 may be a cryo-bag.

Additionally, the first and second containers 402 and 410 may be pressed against each other to form a joint between the remaining portions 424 and 426 of the first and second containers 402 and 410 to form the sample access assembly 400. The steps of: (1) separating the portions 420 and 422 of the first and second containers 402 and 410, and (2) aligning the remaining portions 424 and 426, and (3) coupling the remaining portions 424 and 426 may be carried out while the separating component 427 is still at a desirable temperature to prevent undesirable exposure of the sample 409 to an environment outside the first and second containers 402 and 410.

Further, a joint 432 may be formed due to coupling of the interfaces of the remaining portions 424 and 426 of the first and second containers 402 and 410. Moreover, the remaining portions 424 and 426 of the first and second containers 402 and 410 may form first and second compartments 428 and 430 in the sample access assembly 400. In one embodiment, the joint 432 may be a thermal fusion joint, chemical fusion joint, or both. In one example, the thermal fusion joint may be a hermetically sealed joint. The thermal fusion joint may be formed when the portions 420 and 422 of the first and second containers 402 and 410 are separated from the portions 424 and 426 using a separating component 427 in a heated state, and interfaces of the remaining portions 424 and 426 are brought in contact immediately after separating the portions 420 and 422 from the first and second containers 402 and 410. The melted material at the interfaces of the portions 424 and 426 may fuse together to form the thermal joint. Accordingly, it is desirable that material present at least at the interfaces of the portions 424 and 426 be suitable for forming thermal joints. In some embodiments, the first and second containers 402 and 410 or at least the material at the interface of the portions 424 and 426 of the first and second containers 402 and 410 may be made of thermoplastics. Non limiting examples of the thermoplastics may include polyethylene, ethylene vinyl-acetate (EVA), poly vinyl chloride (PVC), polypropylene, nylon, or combinations thereof. Further, the component position frame of the coupling device 200 may be made of polyxymethylene (POM), phenolics, polyether ether ketone (PEEK), nylon, polypropylene, polyphenylene sulfide (PPS), polyethylene terephthalate (PET), and the like.

Additionally, in the sample access assembly 400, the inlet passage 416 may be disposed closer to the first side 404 of the first compartment 402 relative to the outlet passage 418. Consequently, in operation, the inlet passage 416 is closer to the sample 409 as compared to a position of the outlet passage 418 to facilitate mixing of the sample 409 and the growth medium. However, in alternative embodiments, the outlet passage 418 may be disposed relatively closer to the sample 409 than the inlet passage 416 to provide efficient transfer of the sample 409. Further, the growth medium is introduced in the sample access assembly 400 as represented by an arrow 434 via the inlet passage 416. The sample 409 mixed with the growth medium is extracted from the sample access assembly 400 as presented by arrow 436. Further, the outlet passage 418 is used to extract the mixture of the sample and the growth medium (sample mixture) to a collection device.

Moreover, the growth medium is introduced in the sample access assembly 400 at a determined rate. The rate of introduction of the growth medium in the sample access assembly 400 is maintained at a desirable value to facilitate mixing (arrow 439) of the growth medium with the sample. The extraction rate of the sample mixture is substantially similar to the introduction rate of the growth medium in the sample access assembly 400. Further, the rates of introduction and extraction are maintained so as to facilitate mixing of the sample 409 with the incoming growth medium to facilitate efficient transfer of the sample mixture from the sample access assembly 400 to the collection device. However, it may be noted that a relatively high flow rate of the growth medium may undesirably induce shear. Hence, it may be desirable to maintain a rate of introduction of the growth medium that similar to a rate of extraction of the sample mixture does not induce excessive shear on cells. In one embodiment, a volume of the sample transferred out of the sample access assembly 400 may be in a range from about 1 vol. % to about 100 vol. %, 80 vol. % to about 100 vol. %, or 90 vol. % to about 100 vol. %. It may be noted that with efficient mixing, the percentage of the sample transferred out of the sample access assembly 400 may be derived by the volume of the growth medium introduced into the sample access assembly 400. Since the volume of the sample access assembly 400 is constant and assuming that the amount of growth medium that is introduced in the sample access assembly 400 is similar to the amount of the sample mixture that is extracted from the sample access assembly, an equation for the dilution (or recovery of the cells) may be an exponential function. By way of example, with a 1 ml volume of the sample and a 50 ml volume of the growth medium that is introduced in the sample access assembly, in some embodiments, the recovery of the sample from the sample access assembly 400 (with desirable mixing) may be as high as about 99.99%.

Advantageously, the sample access assembly 400 facilitates transfer of the sample 409 from the first container 402, such as a vial or a cryo-vial, to the collection device with minimal operator intervention. Further, the sample access assembly 400 facilitates efficient transfer in terms of recovery of the sample 409 and also in terms of time required for the transfer from the first container 402 to the collection device. Moreover, the sample access assembly 400 facilitates access to the sample 409 in a sterile manner regardless of the environment in which the sample access assembly 400 is disposed.

Figure 10:
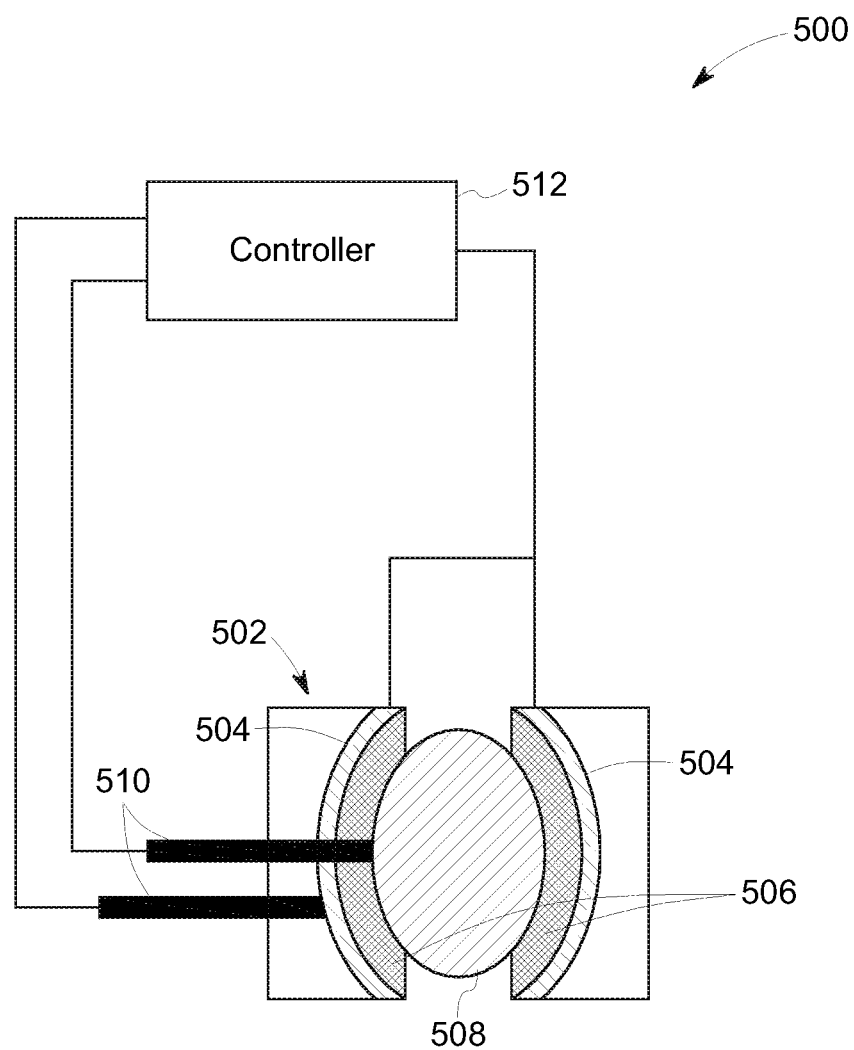
FIG. 10 is a cross-sectional view of a heating component operatively coupled to a first container or a sample access assembly, in accordance with aspects of the present specification.

FIG. 10 illustrates a cross-sectional top view of a portion of a heating assembly 500 having a heating component 502 configured to heat at least a portion of a body 508, such as a first container (not shown in FIG. 10) or a portion of a sample access assembly (not shown in FIG. 10) or a portion of a second container (not shown). By way of example, initially, the heating component 502 may be configured to heat a sample, a sample mixture and/or a growth medium. In a particular example, the sample may be a cryo-preserved sample. In this example, the heating component 502 may be configured to thaw the cryo-preserved sample to form a liquid cell suspension to enable inoculum transfer.

It may be noted that a growth medium is usually stored at about 4° C. However, using the growth medium having a temperature of about 4° C. or below may negatively impact cell growth. Consequently, it may be desirable to pre-warm the growth medium at least to room temperature. In some embodiments, while transferring the sample mixture, the heating component 502 may be used to thaw the cryo-preserved sample as well as warm the growth medium. In one embodiment, the heating component 502 may be used as an inline heater for cold growth medium.

In the illustrated embodiment, the heating component 502 includes a heater 504 and a thermal conductor 506. In one example, the heater 504 may have a flexible and conformable structure. In a non-limiting example, the heater 504 may be a thin film heater. Other non-limiting examples of the heater 504 may include a non-contact heater, such as an infrared (IR) heater, an elastic vessel with temperature-regulated fluid circulating within the vessel, or both.

Further, the thermal conductor 506 may be configured to facilitate uniform transfer of heat from the heater 504 to the body 508. Moreover, the thermal conductor 506 may facilitate uniform distribution of heat to the body 508. Non-limiting examples of the thermal conductor 506 may include a thermally conductive foam and/or rubber doped with thermally conductive particles. Other non-limiting examples of the thermal conductor 506 may include a heated (or a temperature-controlled) bladder which may conform to the first container. In one embodiment, the heating component 502 may be a conformable structure. Further, the heating component 502 may be made of one or more parts. The one or more parts of the heating component 502 may be configured to be conformably disposed around a determined portion of the body 508.

In the illustrated embodiment, the heating assembly 500 may include a temperature sensor 510 that is operatively coupled to the heating component 502 or the body 508. However, in an instance where the heating assembly 500 employs two or more temperature sensors, the two or more temperature sensors may be operatively coupled to both the heating component 502 and the body 508. Consequently, the temperature sensor 510 may be configured to sense a temperature of the heating component and/or the body 508. Non-limiting examples of the temperature sensors 510 may include thermocouples, thermistors, resistance temperature devices (RTDs), or combinations thereof. The heating assembly 500 may further include a temperature controller 512 operatively coupled to the temperature sensors 510 to control a temperature of the heating component 504 and/or the body 508.

Figure 11:
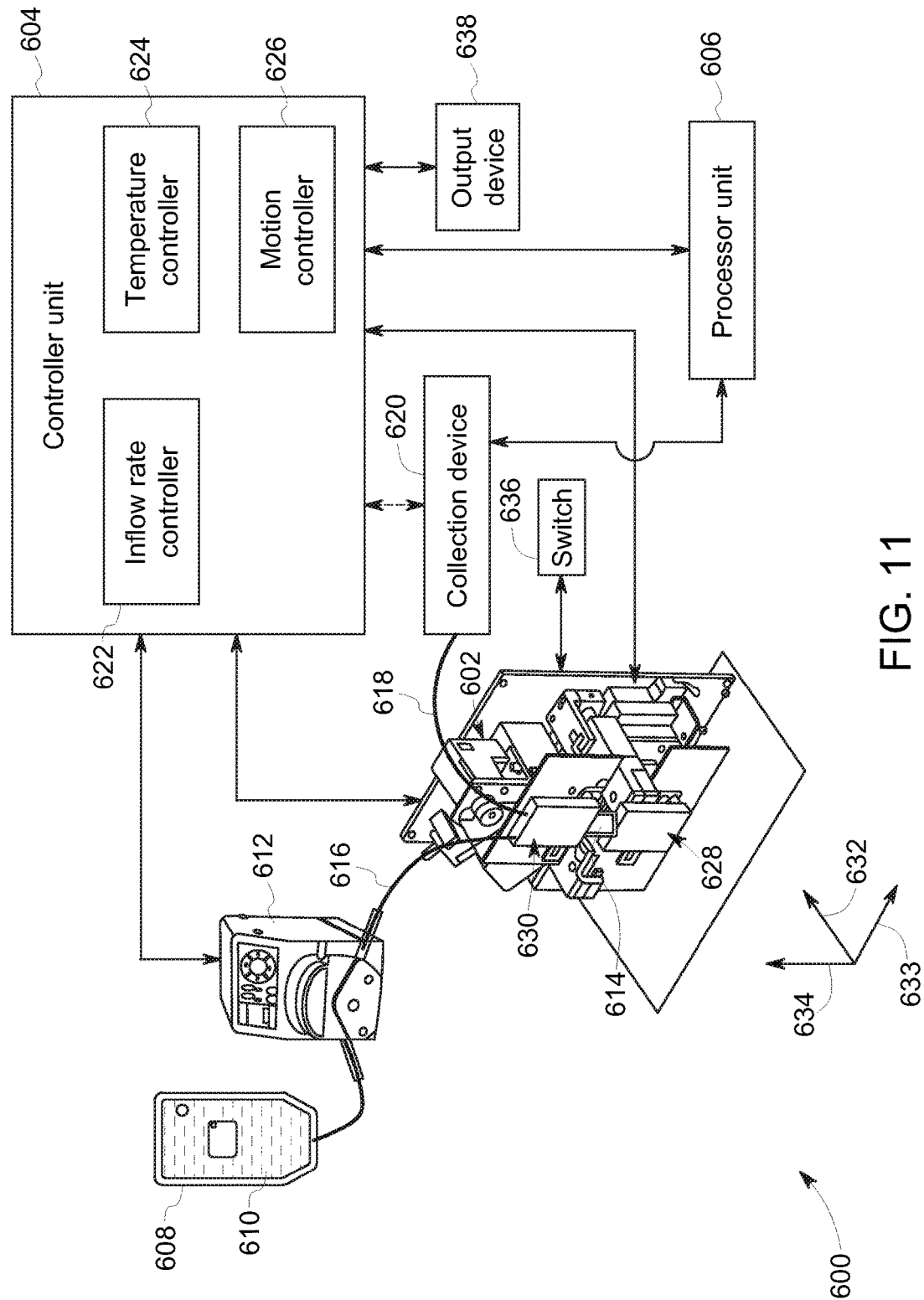
FIG. 11 is a schematic representation of an exemplary automated system for sample transfer, in accordance with aspects of the present specification.

FIG. 11 illustrates an example automated system 600 having a coupling device 602, a controller unit 604 and a processor unit 606. Further, the coupling device 602 is operatively coupled to a growth medium source 608. In particular, the growth medium source 608 may be operatively coupled to a sample access assembly 614 using an inlet passage 616 of the sample access assembly 614. In the illustrated embodiment, the sample access assembly 614 may be configured to receive a growth medium 610 disposed in the growth medium source 608 using a pump 612. In a non-limiting example, the pump 612 may be a peristaltic pump. The pump 612 may be configured to facilitate transfer of the growth medium 610 from the growth medium source 608 to the sample access assembly 614 disposed in the coupling device 602. Further, the pump 612 may be configured to facilitate transfer of the growth medium 610 to the sample access assembly 614 at a determined rate. In particular, the growth medium 610 may be used to flush the contents out of the sample access assembly 614. In particular, in operation, the growth medium 610 may be used to flush the contents out of the first container (not shown in FIG. 11) of the sample access assembly 614.

In some embodiments, the growth medium 610 may be heated to a determined temperature prior to or at the time of transferring the growth medium 610 to the sample access assembly 614. In one embodiment, the determined temperature of the growth medium 610 may be configured to facilitate cell growth in the collection device 620. Further, an outlet passage 618 of the sample access assembly 614 may be operatively coupled to an external device, such as a collection device 620. In some embodiments, the collection device 620 may be configured to receive the sample mixture mixed with the growth medium 610. In a non-limiting example, the collection device may be a bioreactor.

Further, the controller unit 604 may be used to collectively represent various control devices employed in the automated system 600, where the control devices are configured to control and regulate operation of the automated system 600. By way of example, in the illustrated embodiment, the controller unit 604 may be configured to control an input flow of the growth medium 610 using an inflow controller 622.

In addition, one or more temperature controllers 624 may be employed to control a temperature of the sample or sample mixture. In a non-limiting example, the temperature controller 624 may be configured to control the temperature of one or more of a sample disposed in the first container (e.g., a vial), a growth medium 610, and temperature of a heating component (not shown in FIG. 11). It may be noted that in certain embodiments, it may be desirable to thaw the sample before forming the sample access assembly 614.

In some embodiments, additional temperature controllers 624 may be employed to control the temperature of a separating component (not shown in FIG. 11) employed in the coupling device 602. In some embodiments, the controller unit 604 may employ sensors to sense parameters being controlled. By way of example, the controller unit 604 may employ an infrared temperature sensor for sensing a temperature of the separating component, or a thermocouple to sense the temperature of the heating component and/or the sample access assembly 614. Additionally, although not illustrated, in some embodiments, one or more temperature sensors may be operatively coupled to the collection device 620 to sense a temperature of the collection device 620. In one example, thermocouples may be coupled to an external surface of the collection device 620.

Moreover, the controller unit 604 may include a motion controller 626, where the motion controller 626 may be configured to control motion of one or more components of the automated system 600 in one or more directions 632, 633 and 634. In some embodiments, the motion controller 626 may be configured to control a motion of one or more holder units 628 and 630, the separating component, or both.

Further, the processor unit 606 of the automated system 600 may be configured to process data from the controller unit 604. In certain embodiments, the processor unit 606 may also be coupled to one or more user input-output devices (not shown) for receiving commands and inputs from a user. The input-output devices, for example, may include devices such as a keyboard, a touchscreen, a microphone, a mouse, a control panel, a display device, a foot switch, a hand switch, and/or a button. Moreover, the processor unit 606 and/or the controller unit 604 may be configured to be coupled to other devices, such as, but not limited to, the collection device 620, the growth medium source 608, the pump 612, or combinations thereof, to control or monitor the operation of these devices. In one embodiment, the processor unit 606 and the controller unit 604 may be integrated into a single unit.

In an alternative embodiment, each controller of the controller unit 604 may have respective individual processors. In some embodiments, the processor unit 606 and/or the controller unit 604 may be configured to store the related data in a storage repository (not shown). In one embodiment, the storage repository may include devices such as a hard disk drive, a floppy disk drive, a compact disk-read/write (CD-R/W) drive, a digital versatile disc (DVD) drive, a flash drive, and/or a solid-state storage device.

Further, the automated system 600 may include an output device 638 that may be configured to display data representative of the progress of the automated transfer or the automated seed train process, or any other parameters pertinent to the operation of the automated system 600. In one example, the output device 638 may be configured to display the sensed data sensed by one or more sensors employed in the automated system 600.

Advantageously, the automated system 600 may include provisions for simply disposing first and second containers in designated locations in the coupling device 602 and initiating the operation of the coupling device 602, for example, by using a switch 636, to commence transfer of the sample mixture or initiate an automated seed train process. Accordingly, the automated system 600 performs the seed train process with minimal operator intervention, thereby reducing the possibility for human errors and unpredictable results associated therewith. Further, the surrounding environment for the automated system 600 may or may not be sterile. In one embodiment, the first and second containers, the inlet and outlet tubing, and the like may be disposable in nature, thereby making the automated system 600 even less prone to contamination by preventing introduction of contamination from a previous batch, or the like.

Moreover, the automated system 600 may be operated by a non-trained operator. Since the automated system 600 is capable of sterile access of vial contents in a non-sterile environment, a laminar hood or a clean room may not be required, which may significantly reduce floor space requirement and infrastructural cost. Further, the automated system 600 is fully automated and the second container is functionally closed, which significantly lowers of risk of contamination compared to manual process.

In some embodiments, the automated system 600 may be configured to effectively operate in an automated manner. Further, the automated system 600 may be operated in a sterile or a non-sterile environment with same or similar results. In a particular embodiment, where the first container is a cryo-vial, the automated system 600 is configured to receive a frozen or cryopreserved cryo-vial or a pre-thawed or a partially frozen cryo-vial, where the cryo-vial includes a sample having several tens of millions of cells provided by a user. Further, the automated system is configured to thaw the cryo-vial, access and transfer cells from the cryo-vial to a collection device, such as a bioreactor. Advantageously, regardless of the environment in which the automated system is disposed, the system 600 is configured to enable sterile access and transfer of the sample from the cryo-vial to the bioreactor for further processing. In a particular example, the sample in the sample access assembly may be accessed and transferred for culturing the cells to several billion to inoculate a larger-scale bioreactor.

In certain embodiments, the sample access assembly and the automated system employing the sample access assembly for transfer of the sample or the sample mixture may provide an automated production floor solution for biopharmaceutical customers to start with frozen or cryo-preserved vial stock and produce an expanded inoculum ready for the next production vessel (e.g., a bioreactor, such as but not limited to, a WAVE Bag® or Xcellerex® bioreactors).

Furthermore, in certain embodiments, cryo-preserved sample cells disposed in a sample access assembly may be transferred to a suitable culture vessel for cell growth. Further, in these embodiments, the steps beginning with and including the steps of thawing the cryo-preserved sample and ending at the transfer of sample to the suitable culture vessel may be automated. Additionally, the process including the steps of thawing the cryo-preserved sample cells, accessing the sample cells and transferring the sample cells to the suitable culture vessel may be automated with minimal requirement for operator intervention during the process. In one embodiment, the sample access assembly may be a container, such as, but not limited to a cryo-vial. However, in other embodiment, the first container may be a vial, a tube, a pipette, a flask, or any other container configured to house a sample in a sterile environment. Further, in some embodiments, the culture vessel may be employed as an inoculation reactor that serves as a seed source for production scale campaigns. In alternative embodiments, the collection device may be simply a sterilized bag, a sterilized flask, or any other suitable vessel configured to collect the sample. In one embodiment, the collection device may be aseptically coupled to the coupling device prior to the use of the coupling device. Alternatively, the collection device may be pre-coupled to the coupling device. By way of example, the collection device may be pre-coupled to the second container.

Figure 12:
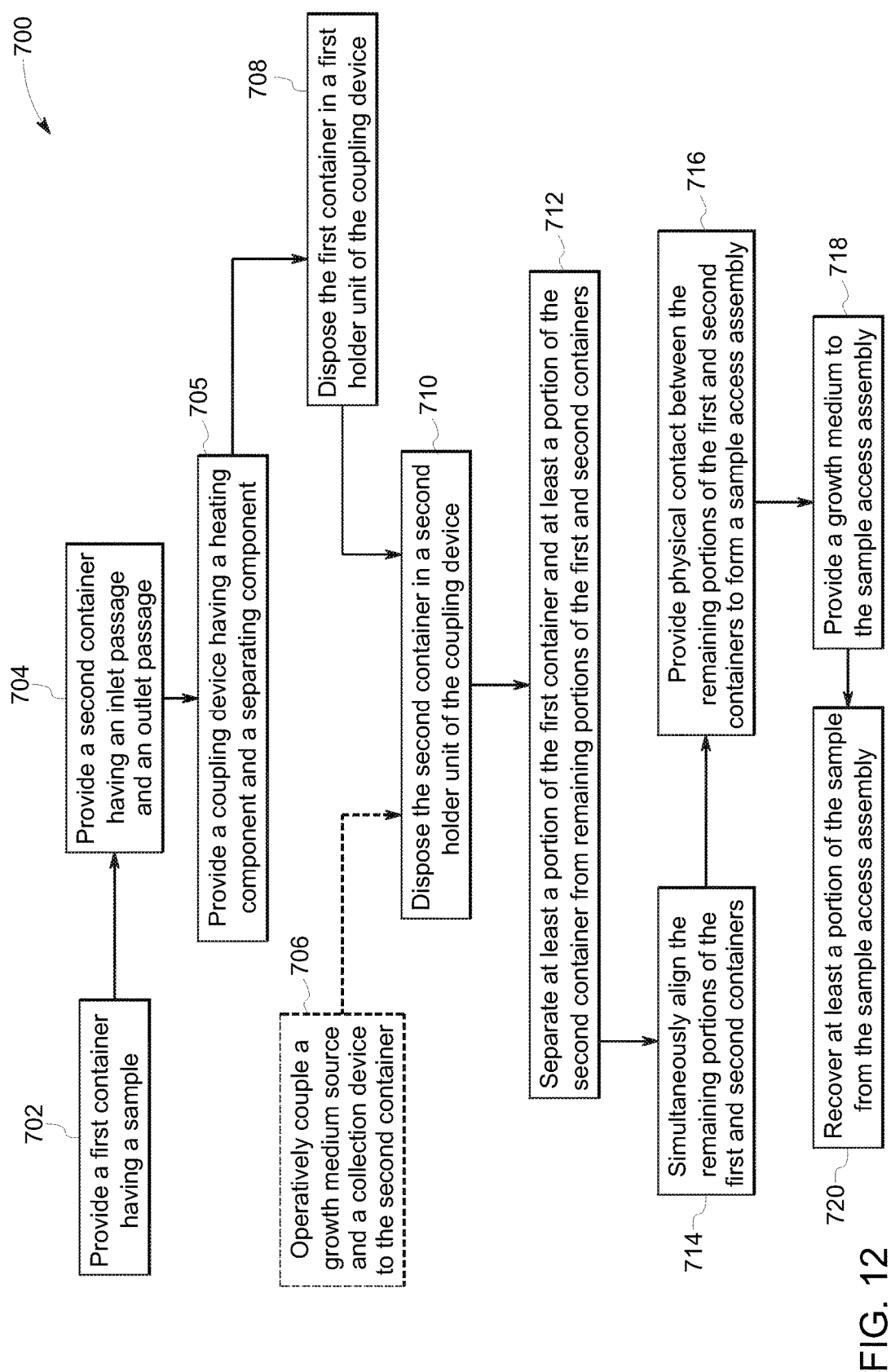
FIG. 12 is a schematic representation of an exemplary flow chart of a method of automated transfer of a sample, in accordance with aspects of the present specification.

FIG. 12 is an exemplary method 700 of automated transfer of a sample, such as a cryo-preserved sample, to a collection device, such as a bioreactor or a flask as a part of seed train process for cell growth or inoculation.

At block 702, the method commences by providing a first container having a sample. The sample may be a cryo-preserved or frozen sample of cells. In one example, the cells may be mammalian cells. The first container may be a vessel containing only the microorganisms of interest, i.e., a cryo-vial or vial with a sample of cells. At block 704, a second container having an inlet passage and an outlet passage may be provided. In one embodiment, the second container may be pre-fitted with an inlet passage and an outlet passage and pre-sterilized.

Further, at block 705 a coupling device having a heating component and a separating component may be provided. Further, the coupling device may include a first holder unit operatively coupled to a heating component and configured for receiving a first container. Moreover, the coupling device may include a second holder unit. In one embodiment, the coupling device may be pre-sterilized.

Optionally, at block 706, the second container may be operatively coupled to one or more external devices, such as, but not limited to a growth medium source, a pump, a collection device, or combinations thereof. Additionally, the second container may also be coupled to the heating component, where the heating component may be configured to pre-heat the growth medium prior to introducing the growth medium in the first container.

Further, at block 708, the first container may be disposed in the first holder unit of the coupling device. In particular, the first container may be disposed in a designated slot in the first holder unit. Further, the heating component may be provided in the slot and the heating component may be configured to be operatively coupled to the first container to heat the sample to a determined temperature before and during transfer of the sample. In a non-limited example, the first container may be a cryo-vial having a cryo-preserved sample. In this embodiment, the heating component may be configured to thaw and heat the cryo-preserved sample, which may initially be at −80° C. or below to a temperature of about 37° C. Alternatively, a water bath or bead bath may be used to heat the sample disposed in the first container before the first container is disposed in the first holder of the coupling device.

In addition, at block 710, the second container may be disposed in the second holder unit of the coupling device. In particular, the second container may be disposed in a respective slot in the second holder unit. In one embodiment, the slot configured to receive the second container may include a heating component. The heating component may be configured to heat the second container and the growth medium passing through the second container to a desired temperature. Consequently, the growth medium introduced to the sample may be at a desirable temperature suitable for inoculation and cell growth.

Moreover, temperature sensors (e.g., thermocouples) may be used to sense the temperature of the first container and/or the heating component. Moreover, a temperature controller may be used to modulate the temperature of the first container or the temperature of the heating component to about 37° C. to thaw the sample. Maintaining the temperature at or below 37° C. ensures that the cells of the sample are not overheated. The heating component may be used to thaw the first container for a determined amount of time depending primarily on a size of the first container. In some embodiments, the heating component may be configured to rapidly thaw the first container while maintaining cell viability and growth comparable to conventionally used but time consuming procedures such as, a water bath and a bead bath.

Moreover, at block 712, after disposing the first and second containers in their respective slots, portions of the first and second containers may be separated from remaining portions of the first and second containers using the separating component.

Further, at block 714, immediately after the separation of portions of the first and second containers, remaining portions of the first and second containers may be aligned. Also, at block 716 during or immediately following the separating step, the remaining portions of the first and second containers may be pressed against each other to physically couple the remaining portions to form a sample access assembly while or after separating component is retracted. In one embodiment, where a heated blade is used as the separating component, the remaining portions may be thermally fused. However, in alternative embodiments, other coupling techniques may also be employed.

In addition, at block 718, after the formation of the sample access assembly, the growth medium may be provided to the sample access assembly and subsequently to the collection device operatively coupled to the sample access assembly. In a particular example, after forming the sample access assembly, the peristaltic pump may be turned on to provide the growth medium through the sample access assembly into the bioreactor. Efficient mixing of the growth medium and the sample is facilitated by the design of the sample access assembly, such as positioning of the inlet and outlet passages, and dimensions of the inlet passages disposed inside the sample access assembly, to maximize recovery of the sample.

In certain embodiments, the flow rate of the growth medium and the amount of growth medium to be provided to the sample access assembly may be calculated based on one or more of: 1) desirable cell recovery, 2) desirable shear, and 3) desirable cell density in the sample mixture to inoculate the next expansion. Further, the flow rate of the growth medium may be so as to prevent excessive shear on the cells and ensure good mixing. Consequently, at block 720, the sample may be efficiently recovered from the sample access assembly and transferred from the sample access assembly to the collection device.

Further, steps 712 to 718 or 712 to 720 may be performed with minimal information provided to the system by the operator. By way of example, the operator may only be required to input the vial type and/or desirable volume of the sample in the vial. In some embodiments, assuming that the collection device is already connected to the second container, there may be no further operator intervention required for the steps of the forming the sample access assembly once the first and second containers have been provided. The system may be automated from the step of heating the sample till the step of transferring of the sample mixture to the collection device. Alternatively, a minimal operator intervention that may be required after formation of the sample access assembly entails operating a switch to power the pump and the other components involved in the transfer of the sample mixture to the collection device.

Further, the steps 702-720 of the method described in the flow chart 700 may or may not be conducted in the same order as illustrated. By way of example, the second container may be provided before the first container, or the growth medium source may be pre-coupled prior to disposing the second container in the coupling device.

Advantageously, the devices, systems and method of sample transfer are designed to be flexible, easy to operate and infrastructure friendly (e.g., there is no need for a sterile environment). Further, the automated system may be placed either on a bench or a cart, thereby increasing the flexibility of the entire cell production floor. Also, the automated system may not require a skilled person to operate the system. Moreover, disposable nature of the sample access assembly and the collection device allows for rapid change over in the production facility. Moreover, the systems and methods of the present specification are automated to a large extent after installation of the first and second containers and are thus less labor intensive.

While only certain features of the disclosure have been illustrated and described herein, many modifications and changes will occur to those skilled in the art. It is, therefore, to be understood that the appended claims are intended to cover all such modifications and changes as fall within the true spirit of the disclosure.

The invention claimed is:

1. A coupling device configured to form a sample access assembly using first and second containers, wherein the sample access assembly comprises a first compartment and a second compartment, and wherein the sample access assembly is configured to house a sample, the coupling device comprising:
a heating component configured to heat at least a portion of the sample; and
a separating component configured to separate at least a portion of the first container and at least a portion of the second container from remaining portions of the first and second containers to form the first and second compartments of the sample access assembly,
wherein the coupling device is configured to transfer at least a portion of the sample, and wherein the coupling device is configured to maintain a sterile environment for the sample at least during coupling of the first and second compartments; and
wherein the coupling device is configured such that coupling the first and second compartments to form the sample access assembly comprises thermally fusing interfaces of the first and second compartments.

2. The coupling device of claim 1, wherein the first and second compartments are respective portions of the first and second containers.

3. The coupling device of claim 2, further comprising:
a first holder unit configured to receive at least a portion of the first container, wherein the first container is configured to receive the sample; and
a second holder unit operatively coupled to the first holder unit, wherein the second holder unit is configured to receive at least a portion of the second container, wherein the first and second holder units comprise one or more degrees of freedom, and wherein the first and second holder units are configured to align the portions of the first and second containers using the one or more degrees of freedom to form the sample access assembly while maintaining the sterile environment to the sample.

4. The coupling device of claim 3, wherein the heating component is operatively coupled to the first holder unit.

5. The coupling device of claim 3, wherein the heating component is disposed in the first holder unit, the second holder unit, or both.

6. The coupling device of claim 1, wherein the second container comprises an inlet passage, an outlet passage, or both.

7. The coupling device of claim 6, wherein at least a portion of the sample disposed in the first compartment is accessible via the inlet passage, the outlet passage, or both.

8. The coupling device of claim 1, wherein the first and second compartments are fused to form the sample access assembly.

9. The coupling device of claim 1, wherein the first container is a cryo-vial.

10. The coupling device of claim 1, wherein the separating component is a blade.

11. The coupling device of claim 10, wherein a thickness of the blade is in a range from about 0.01 inch to about 0.03 inch.

12. The coupling device of claim 1, wherein the heating component comprises a multilayered structure.

13. The coupling device of claim 12, wherein the multilayered structure comprises a thin film heater.

14. The coupling device of claim 1, wherein the heating component comprises a thin film heater and a thermally conductive foam operatively coupled to the thin film heater.

15. The coupling device of claim 1, further comprising a temperature sensor, a temperature controller, or both, wherein the temperature sensor and the temperature controller are operatively coupled to at least one of the first compartment, the second compartment, the heating component, the separating component, and combinations thereof.

16. An automated system for sample transfer, comprising:
a coupling device configured to form a sample access assembly using first and second containers, wherein the sample access assembly comprises a first compartment and a second compartment, and wherein the sample access assembly is configured to house a sample, the coupling device comprising:
a heating component configured to heat at least a portion of the sample;
a separating component configured to separate at least a portion of the first container and at least a portion of the second container from remaining portions of the first and second containers to form the first and second compartments,
wherein the coupling device is configured to transfer at least a portion of the sample, and wherein the coupling device is configured to maintain a sterile environment for the sample at least during coupling of the first and second compartments,
a collection device operatively coupled to an outlet passage of the second compartment to receive at least a portion of the sample; and
wherein the coupling device is configured such that coupling the first and second compartments to form the sample access assembly comprises thermally fusing interfaces of the first and second compartments.

17. The automated system of claim 16, further comprising a growth medium source operatively coupled to an inlet passage of the second compartment.

18. The automated system of claim 17, further comprising a pump configured to regulate a flow of a growth medium from the growth medium source to the sample access assembly.

19. A method for automated sample transfer, comprising:
providing a coupling device having first and second holder units;
disposing a first container having a sample in the first holder unit of the coupling device;
disposing a second container having an inlet passage and an outlet passage in the second holder unit of the coupling device;
separating at least a portion of the first container and at least a portion of the second container from remaining portions of the first and second containers to form first and second compartments;
coupling the first and second compartments to form a sample access assembly;
heating at least a portion of the sample to a determined temperature; and
transferring at least a portion of the sample from the sample access assembly to a collection device;
wherein the step of coupling the first and second compartments to form the sample access assembly comprises thermally fusing interfaces of the first and second compartments.

20. The method of claim 19, wherein the step of separating at least the portion of the first container and at least the portion of the second container to form the first and second compartments comprises:
heating a separating element disposed in the coupling device to a determined temperature; and
separating the portions of the first and second containers using the separating component.

21. The method of claim 20, wherein the step of heating at least the portion of the sample comprises thawing at least the portion of the sample using a heating element disposed in the first holder unit.

22. The method of claim 19, wherein the step of heating the portion of the sample comprises thawing the portion of the sample using a heating element disposed in the first holder unit.

23. The method of claim 19, further comprising:
operatively coupling the inlet passage of the second container to a growth medium source; and
operatively coupling the collection device to the outlet passage of the second container,
wherein the growth medium source and the collection device are coupled to the second container prior to disposing the second container in the second holder unit of the coupling device.

* * * * *